US008753289B2

(12) United States Patent
Konya et al.

(10) Patent No.: US 8,753,289 B2
(45) Date of Patent: Jun. 17, 2014

(54) PRICKING SYSTEM

(75) Inventors: Ahmet Konya, Waldsee (DE); Herbert Harttig, Neustadt (DE)

(73) Assignee: Roche Diagnostics Operations, Inc., Indianapolis, IN (US)

(*) Notice: Subject to any disclaimer, the term of this patent is extended or adjusted under 35 U.S.C. 154(b) by 970 days.

(21) Appl. No.: 12/619,420

(22) Filed: Nov. 16, 2009

(65) Prior Publication Data

US 2010/0094325 A1 Apr. 15, 2010

Related U.S. Application Data

(63) Continuation of application No. PCT/EP2008/003242, filed on Apr. 23, 2008.

(30) Foreign Application Priority Data

May 16, 2007 (EP) .................................... 07009744

(51) Int. Cl.
A61B 5/00 (2006.01)
A61B 17/14 (2006.01)
A61B 17/32 (2006.01)

(52) U.S. Cl.
USPC ........... 600/573; 600/583; 600/584; 606/181; 606/182

(58) Field of Classification Search
USPC ........... 600/582–583, 573, 584; 606/181–184
See application file for complete search history.

(56) References Cited

U.S. PATENT DOCUMENTS 4,416,279 A 11/1983 Lindner et al.
4,442,836 A 4/1984 Meinecke et al.
(Continued)

FOREIGN PATENT DOCUMENTS

CA 2311496 A1 6/1999
DE 19705091 A1 2/1999
(Continued)

OTHER PUBLICATIONS

English Translation of corresponding PCT/EP2008/003242 Written Opinion.

Primary Examiner — Rene Towa
Assistant Examiner — May Abouelela
(74) Attorney, Agent, or Firm — Bose McKinney & Evans LLP

(57) ABSTRACT

A pricking system includes lancets for producing a prick wound, sampling devices for collecting a sample of a body fluid from the prick wound, a housing having an opening for application of a body part in which the prick wound is to be produced, a drive arranged in the housing for moving one of the lancets to produce the prick wound and to then move one of the sampling devices to the prick wound so produced, a coupling part for coupling to the drive one of the lancets for a pricking movement and then coupling to the drive one of the sampling devices for a sampling movement, the coupling part being moved, during the pricking movement and the sampling movement, respectively, from a starting position into an end position by an advancing movement, and from the end position back into the starting position by a reversing movement, respectively, and a motion control which, during the sampling movement, causes the coupling part to reach an end position that differs from the end position reached by the coupling part during the pricking movement, wherein the end position reached by the coupling part in the sampling movement is laterally displaced relative to the end position reached by the coupling part in the prickling movement.

12 Claims, 7 Drawing Sheets

(56) References Cited

U.S. PATENT DOCUMENTS

| | | | |
|---|---|---|---|
| 5,508,171 A | 4/1996 | Walling et al. | |
| 5,554,166 A | 9/1996 | Lange et al. | |
| 5,846,837 A | 12/1998 | Thym et al. | |
| 6,036,919 A | 3/2000 | Thym et al. | |
| 6,322,575 B1* | 11/2001 | Schraga | 606/181 |
| 6,472,220 B1* | 10/2002 | Simons et al. | 436/63 |
| 7,008,799 B1 | 3/2006 | Zimmer et al. | |
| 7,025,774 B2* | 4/2006 | Freeman et al. | 606/181 |
| 7,223,248 B2* | 5/2007 | Erickson et al. | 600/584 |
| 7,238,192 B2 | 7/2007 | List et al. | |
| 7,344,507 B2* | 3/2008 | Briggs et al. | 600/583 |
| 7,377,904 B2* | 5/2008 | Conway et al. | 600/583 |
| 7,479,119 B2* | 1/2009 | Roe | 600/584 |
| 7,481,777 B2* | 1/2009 | Chan et al. | 600/583 |
| 7,654,969 B2* | 2/2010 | Wong et al. | 600/583 |
| 7,862,519 B1* | 1/2011 | Ward et al. | 600/583 |
| 8,540,647 B2* | 9/2013 | Konya | 600/583 |
| 2002/0052618 A1* | 5/2002 | Haar et al. | 606/181 |
| 2002/0188224 A1* | 12/2002 | Roe et al. | 600/584 |
| 2003/0050573 A1* | 3/2003 | Kuhr et al. | 600/567 |
| 2003/0050655 A1* | 3/2003 | Roe | 606/182 |
| 2003/0083686 A1* | 5/2003 | Freeman et al. | 606/181 |
| 2003/0211619 A1* | 11/2003 | Olson et al. | 436/44 |
| 2003/0216767 A1 | 11/2003 | List et al. | |
| 2004/0138688 A1* | 7/2004 | Giraud | 606/181 |
| 2004/0225312 A1* | 11/2004 | Orloff et al. | 606/182 |
| 2004/0254599 A1* | 12/2004 | Lipoma et al. | 606/181 |
| 2005/0015020 A1* | 1/2005 | LeVaughn et al. | 600/583 |
| 2005/0023448 A1 | 2/2005 | Ogawara et al. | |
| 2005/0177183 A1* | 8/2005 | Thorne et al. | 606/167 |
| 2005/0201897 A1* | 9/2005 | Zimmer et al. | 422/82.05 |
| 2005/0232815 A1 | 10/2005 | Ruhl et al. | |
| 2005/0245845 A1* | 11/2005 | Roe et al. | 600/583 |
| 2005/0245954 A1* | 11/2005 | Roe et al. | 606/181 |
| 2006/0002816 A1 | 1/2006 | Zimmer et al. | |
| 2006/0052724 A1* | 3/2006 | Roe | 600/583 |
| 2006/0100542 A9* | 5/2006 | Wong et al. | 600/583 |
| 2006/0173380 A1* | 8/2006 | Hoenes et al. | 600/583 |
| 2006/0216817 A1 | 9/2006 | Hoenes et al. | |
| 2006/0229533 A1* | 10/2006 | Hoenes et al. | 600/584 |
| 2006/0247554 A1* | 11/2006 | Roe | 600/583 |
| 2006/0247555 A1* | 11/2006 | Harttig | 600/584 |
| 2007/0004990 A1* | 1/2007 | Kistner et al. | 600/583 |
| 2007/0038150 A1* | 2/2007 | Calasso et al. | 600/583 |
| 2007/0173740 A1* | 7/2007 | Chan et al. | 600/583 |
| 2007/0179406 A1 | 8/2007 | DeNuzzio et al. | |
| 2007/0219572 A1* | 9/2007 | Deck et al. | 606/181 |
| 2008/0103415 A1* | 5/2008 | Roe et al. | 600/583 |
| 2008/0161725 A1* | 7/2008 | Wong et al. | 600/583 |
| 2009/0321287 A1* | 12/2009 | List et al. | 206/223 |
| 2010/0210970 A1* | 8/2010 | Horikawa et al. | 600/583 |
| 2010/0222703 A1* | 9/2010 | Takashima et al. | 600/583 |
| 2012/0226195 A1* | 9/2012 | Chan et al. | 600/583 |

FOREIGN PATENT DOCUMENTS

| | | |
|---|---|---|
| DE | 10332488 A1 | 2/2005 |
| DE | 10343896 A1 | 4/2005 |
| EP | 1424040 A1 | 11/2002 |
| EP | 1402812 B1 | 3/2006 |
| EP | 1714613 A1 | 10/2006 |
| KR | 20060023591 A1 | 3/2006 |
| WO | 97/02487 A1 | 1/1997 |
| WO | 98/48695 A1 | 11/1998 |
| WO | 2004/056269 A1 | 7/2004 |
| WO | 2004/060143 A1 | 7/2004 |
| WO | 2005/020197 A1 | 3/2005 |
| WO | 2005/107596 A2 | 11/2005 |
| WO | 2006/013045 A1 | 2/2006 |

* cited by examiner

PRICKING SYSTEM

CROSS-REFERENCES TO RELATED APPLICATIONS

This application is a continuation of International Patent Application No. PCT/EP2008/003242, filed Apr. 23, 2008, which claims priority to European Application No. 07009744.9, filed. May 16, 2007.

FIELD OF THE INVENTION

The present invention relates to the field of pricking systems.

DESCRIPTION OF RELATED ART

Pricking systems are used, for example, by diabetics who have to check their blood-sugar level several times a day and who need for that purpose a sample of body liquid, as a rule of blood or interstitial liquid that is gained from a prick wound produced by a pricking system.

Especially high user comfort is offered by pricking systems where one and the same appliance is used for producing a prick wound and for collecting a sample from a prick wound so produced. Automatic sampling makes it easier for a user to analyze a sample of body liquid, which is a considerable advantage especially for persons whose manual mobility is impaired by age or illness. In addition, automatic sampling reduces the risk of contamination of samples, which otherwise might lead to distortion of the measuring results.

However, automatic sampling provides the risk that too small a portion of the body liquid issuing from the prick wound, insufficient to guarantee reliable testing, may be collected. In the worst of all cases this may lead to the result that following an unsuccessful sampling test a user has to undergo a second pricking operation. In order to reduce the risk of unsuccessful pricking, i.e. that an insufficient quantity of sampling liquid is collected, it normally is possible to increase the pricking depth so that a greater quantity of body liquid will issue from the prick wound. While in this way the probability of a sufficient quantity of body liquid being withdrawn from the prick wound can be increased, a greater pricking depth causes greater pain.

Now, it is an object of the present invention to show how the collection of samples can be improved for a pricking system.

That object is achieved by a pricking system having the features defined in claim 1. Advantageous further developments are the subject matter of the dependent claims.

BRIEF SUMMARY OF THE INVENTION

It is against the above background that the present invention provides certain unobvious advantages and advancements over the prior art. In particular, the inventors have recognized a need for improvements in pricking systems. In accordance with one embodiment of the present invention, a drive of the pricking system is coupled, via a coupling element, with a lancet for a pricking movement and with a sampling device for a sampling movement. Accordingly, the coupling part is moved during each pricking movement and each sampling movement, respectively, from a starting position to an end position by an advancing movement, and then back from the end position to the starting position by a reversing movement.

Although the sampling device should be guided for a sampling operation as precisely as possible to the prick wound that has been produced before by a pricking movement, it has been found as part of the invention that identical movements of the coupling part in a sampling movement and a pricking movement are neither necessary nor advantageous. Surprisingly, efficient sampling can be achieved when the end position reached by the coupling part in a sampling movement differs from the end position reached by the coupling part in a pricking movement.

This can be achieved by having the coupling part perform a longer travel in a sampling movement than in a pricking movement. It is possible in this way to adjust the travel of a pricking movement to the particular pricking depth that meets the requirements of a user and to neverthe less guarantee at any time reliable sampling.

Alternatively or additionally, there is the possibility, with a view to improving the efficiency of the sampling operation, to laterally offset the end position reached by the coupling part in a sampling movement, also and especially relative to an end position that is reached by the coupling part in, a pricking movement.

These and other features and advantages of the present invention will be more fully understood from the following detailed description of the invention taken together with the accompanying claims. It is noted that the scope of the claims is defined by the recitations therein and not by the specific discussion of features and advantages set forth in the present description.

BRIEF DESCRIPTION OF THE SEVERAL VIEWS OF THE DRAWING

The following detailed description of the embodiments of the present invention can be best understood when read in conjunction with the following drawing. In the drawing, identical and corresponding components are indicated by the same reference numerals, where like structure is indicated with like reference numerals and in which.

Skilled artisans will appreciate that elements in the figures are illustrated for simplicity and clarity and have not necessarily been drawn to scale. For example, the dimensions of some of the elements in the figures may be exaggerated relative to other elements to help improve understanding of the embodiments of the present invention.

DETAILED DESCRIPTION OF THE INVENTION

For the purposes of describing and defining the present invention it is noted that terms like "preferably", "commonly", and "typically" are not utilized herein to limit the scope of the claimed invention or to imply that certain features are critical, essential, or even important to the structure or function of the claimed invention. Rather, these terms are merely intended to highlight alternative or additional features that may or may not be utilized in a particular embodiment of the present invention.

Figure 1:
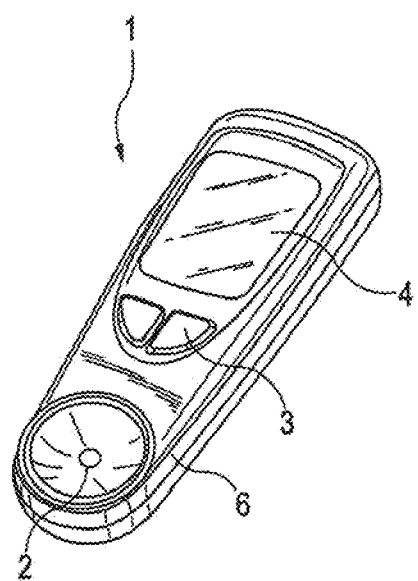
FIG. 1 shows an embodiment of a pricking system according to the invention.

FIG. 1 shows one embodiment of a lancing instrument 1 according to the invention intended for collecting a sample of a body liquid. The lancing instrument 1 comprises a housing 6 with a housing opening 2 against which a body area is pressed for producing a prick wound. Further, the lancing instrument 1 comprises operating elements 3 in the form of keys and a display 4 in the form of a liquid crystal display intended for displaying examination results.

In the illustrated embodiment, the pricking system 1 comprises a multiple-use pricking device into which an exchangeable supply of lancets and test elements can be loaded. For this purpose, the pricking device is equipped with a receptacle (not shown) for an exchangeable supply of lancets and test elements. The receptacle has an opening that can be closed, arranged on the back of the embodiment illustrated in FIG. 1. However, there is also the possibility to realize the pricking device without the possibility to exchange the lancet supply so that the pricking device has to be discarded once the lancet supply contained in it has been used up.

The supply of lancets and test elements of the illustrated embodiment consists in a carrier tape which carries a plurality of lancets between which test elements are arranged for examination of a sample of a body liquid. The test elements contain for example test chemicals which, when brought into contact with an analyte to be detected, for example glucose, produce a change in color that can be recorded photometrically. Electrochemical sample testing, for example, is likewise possible.

The carrier tape is moved by a transport facility in a feed direction so that the lancets and test elements can be sequentially moved to the correct position for use. The transport facility may comprise, for example, a winding device on which the carrier strip is wound up in a manner similar to a tape of a tape cassette. Instead of using a carrier tape as a supply of lancets and test elements, other kinds of lancet and/or test element supplies, such as rotary magazines, may be used as well.

The term "transport direction" as used herein is understood to describe the longitudinal direction of the carrier tape along which the carrier tape must be transported to move unused lancets to the pricking position, and to remove used lancets from the pricking position.

FIGS. 2 to 5 show by way of a diagrammatic representation the manner in which a prick wound is produced by a lancet 7 in a body part 5 brought into contact with the housing opening 2 and, thereafter, a body liquid 8 issuing from the prick wound is collected using a sampling device 9. In the illustrated embodiment, the sampling device 9 comprises a test field which, just the lancet 7 used for producing the prick wound, is arranged on a carrier tape 10.

Figure 2:
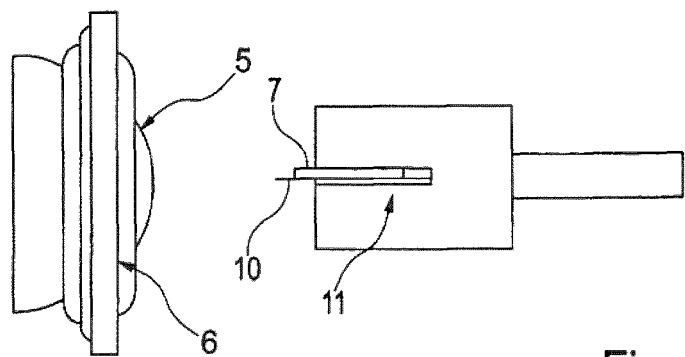
FIG. 2 shows a diagrammatic representation of the position of a coupling part with a lancet, relative to a body part brought into contact with an appliance opening, prior to a pricking operation.

FIG. 2 shows a body part 5, that has been brought into contact with the housing opening 2, and a coupling part 11 which couples with a drive a lancet 7 for a pricking movement and, following the latter, a sampling device 9 for a sampling movement. The illustrated coupling part 11 is provided with a gap through which is guided the carrier tape, carrying the lancets 7 and the test fields 9. In the illustrated embodiment, the lancets 7 are arranged transversely to the longitudinal direction of the carrier tape 10. FIG. 2 shows a cross-sectional view of the coupling part 11 and the carrier tape 10, with a lancet 7 located in the correct position for use, in which it can be moved together with the coupling part 11 for performing a pricking movement.

Figure 3:
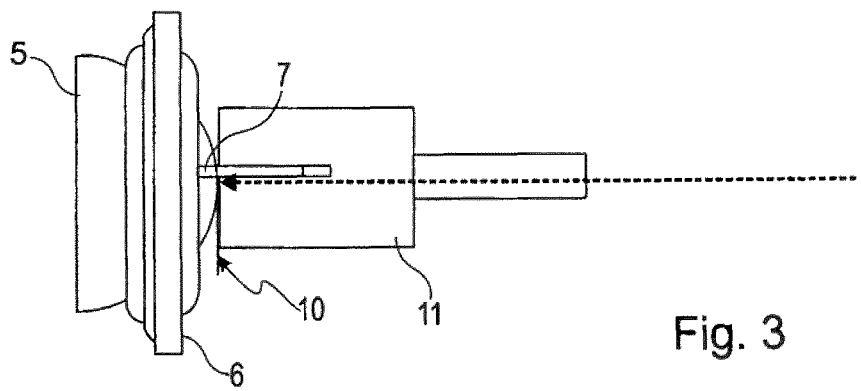
FIG. 3 shows a representation according to FIG. 2, at the moment a body part is pricked by the lancet.

At the moment of a pricking movement, the coupling part 11 is moved in a pricking direction, which is indicated in FIG. 3 by a broken line. During the pricking movement, the carrier tape 10 is bent in lengthwise direction so that the tip of the lancet 7 is lifted off the carrier tape 10 and pricks the body part 5 applied to the housing opening 2, as illustrated in FIG. 3.

The term "bending in lengthwise direction" as used in this connection is meant to describe that the carrier tape is bent about a geometric bending axis that extends in lengthwise direction of the strip. Bending of the carrier tape in lengthwise direction, accordingly, has the effect that the two longitudinal edges of the carrier tape come to include between them an angle different from 180°, for example an angle of between 90° and 135°.

The pricking movement comprises an advancing movement by which the coupling part 11 is moved from the starting position illustrated in FIG. 2 to the end position illustrated in FIG. 3. In a second part of the pricking movement, the coupling part 11 is returned by a reversing movement to a starting position for a sampling movement. The starting position for a sampling movement is illustrated in FIG. 4 and, preferably, is identical to the starting position for a pricking movement illustrated in FIG. 2.

Figure 4:
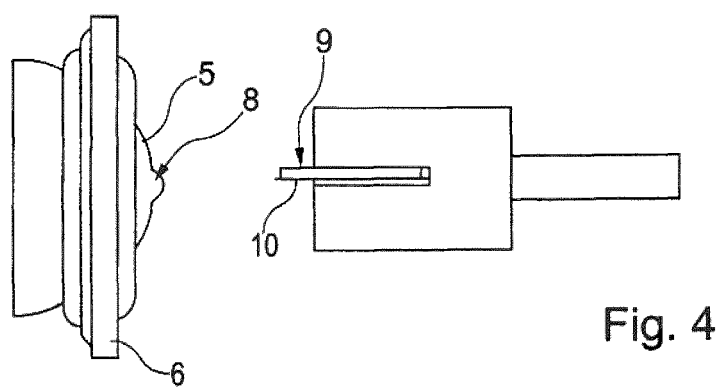
FIG. 4 shows a representation according to FIG. 2, prior to a sampling operation.

Body liquid 8 issuing from a prick wound produced is illustrated diagrammatically as drops in FIG. 4. For collecting body liquid 8, one uses a sampling device 9, preferably a test field, which in the illustrated embodiment is likewise arranged on the carrier tape 10. A transport movement of the carrier 10 transversely to the pricking direction moves a test field 9 into the pricking position in the gap of the coupling part 11 where the lancet 7 was located before.

Figure 5:
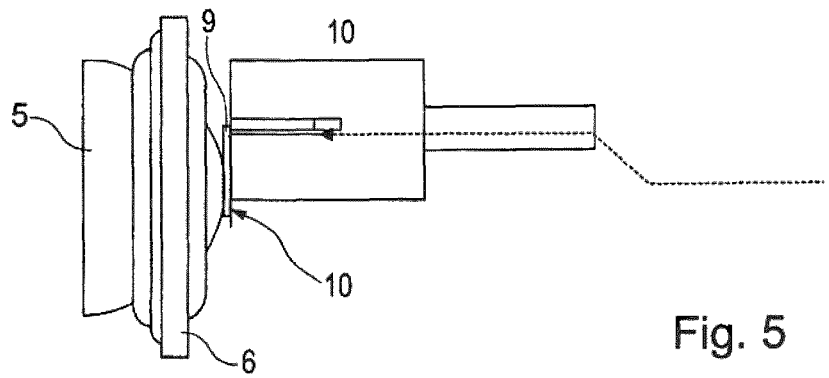
FIG. 5 shows a representation according to FIGS. 2 to 4 at the moment of a sampling operation.

During collection of a sample, the carrier tape 10 is bent in its lengthwise direction, just as it was during the pricking operation. The sampling movement is illustrated in FIG. 5 by a broken line. A comparison with FIG. 3 reveals that the sampling movement differs from the pricking movement. During the advancing step of a sampling movement the coupling part 11 is deflected laterally so that it reaches an end position, illustrated in FIG. 5, laterally offset relative to the end position illustrated in FIG. 3, which is reached by the coupling part during a pricking movement. That lateral offset transversely to the pricking direction has the effect that the prick wound gets into contact with the carrier tape 10 on an extended surface area, bent in its lengthwise direction, and accordingly with the sampling device 9 arranged on the carrier tape 10, namely a test field. This ensures reliable collection of a sample of a body liquid.

If the coupling part 11 were to reach the same end position by the sampling movement as by a pricking movement, i.e. the end position illustrated in FIG. 3, then the carrier tape 10, being bent in lengthwise direction, would touch the prick wound only by its bending edge. Even the smallest movement of the body part 5 could then have the result that the relative position of the prick wound between the pricking movement and the sampling movement could slightly change and the bending edge of the carrier tape 10 could come to be spaced from the prick wound a sufficient amount to cause body liquid from being picked up either not at all, or in insufficient quantity. That risk does not exist in the case of a sampling movement, as illustrated in FIG. 5, the prick wound being contacted in this case by the bent-over carrier tape 10 over its full surface so that a sample of a body liquid 8 can be picked up reliably, even in case of some positioning inaccuracy that might result, for example, from movements of the body part 5 relative to the housing 6.

The lateral offset of the coupling part 11 preferably amounts to more than 1 mm so that positioning inaccuracies of the sampling device 9 or movements of the body part 5 are of no significance, if possible. In principle, improved sample collection may, however, also be achieved with a lateral offset, i.e. transversely to the pricking direction, of less than 1 mm.

Figure 6:
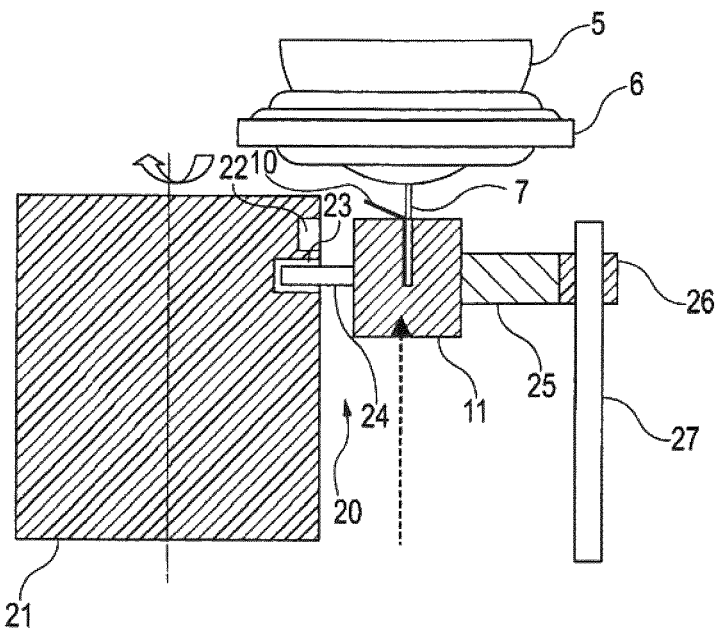
FIG. 6 shows a diagrammatic representation, of an embodiment of a motion control adapted to generate different motion profiles for the coupling part.

FIG. 6 shows an embodiment of a motion control 20 by which different motion profiles of the coupling part 11 can be achieved for the pricking movement and the sampling movement, respectively. In FIG. 6, the coupling part 11 is illustrated together with the drive 21 at the time a body part 5, applied to the housing opening 2, is being pricked. The drive 21 comprises a rotor with two grooves 22, 23 of different depths disposed on a cylindrical lateral surface of the rotor. The two grooves 22, 23 each constitute a cam. Cams of that type are also described as slotted link.

The coupling part 11 comprises a cam rider 24 that moves along the deeper groove 23 during a pricking movement, as illustrated in FIG. 6. The coupling part 11 is urged against the rotor 21 by a spring 25 so that the cam rider 24 will always be fully engaged in the cam 22, 23. In the deeper groove 23 the cam rider 24 is not loaded by the spring 25 in order to ensure that as little friction as possible will occur during a pricking movement. The spring 25 is supported on a guide 26, which is movable in the pricking direction and which in the illustrated embodiment is configured as a guide carriage adapted to movably slide along a rod or guide (27) extending in the pricking direction.

Figure 7:
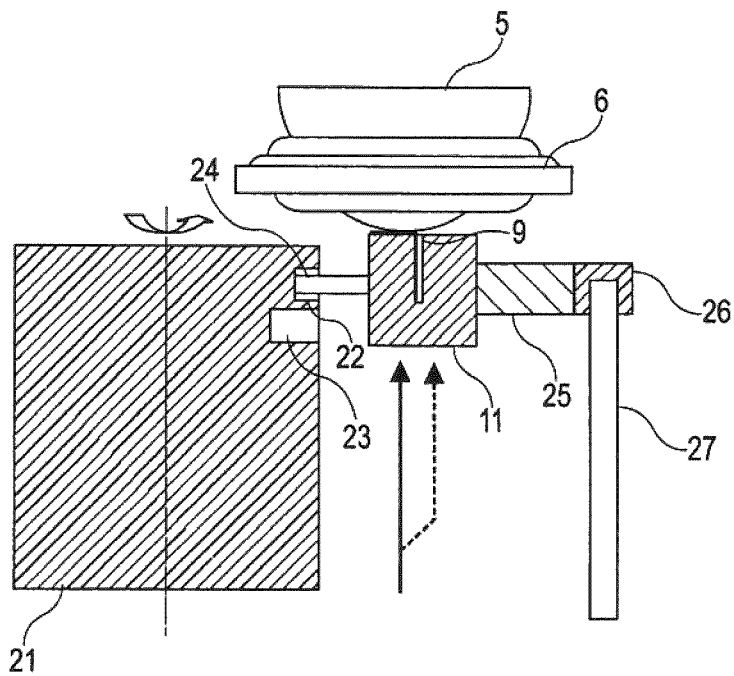
FIG. 7 shows the embodiment illustrated in FIG. 6, at the moment of a sampling operation.

FIG. 7 shows the example illustrated in FIG. 6 in a sampling movement where the cam rider 24 engages the groove 22 of lesser depth. Accordingly, the end position of a sampling movement of the coupling part 11, illustrated in FIG. 7, is laterally displaced compared with the end position of the pricking movement illustrated in FIG. 6, i.e. offset transversely to the pricking direction. The end position reached by the coupling part 11 in a sampling movement differs in the illustrated embodiment from the end position reached in a pricking movement, additionally with respect to the pricking direction. For greater clarity, both the pricking movement and the sampling movement are indicated by arrows in FIG. 7.

In that embodiment, the travel of the coupling part 11 is greater in a sampling movement than in a pricking movement, the groove 22 of lesser depth extending above the groove 23 in the pricking direction. This is of advantage because the travel during a pricking movement may depend on the pricking depth that may be adjusted, for example, by varying the spacing between the housing opening 2 and the drive 21. Generally, it can be said that the travel of a pricking movement gets smaller as the adjusted pricking depth decreases. However, the position of the skin surface, from which a sample of a body liquid 8 is to be picked up by the sampling movement, relative to the housing opening 2 does not depend on the pricking depth. By making the travel of the coupling part 11 greater for a sampling movement than for a pricking movement, reliable sample collection can be ensured also for different pricking depths.

In the illustrated embodiment, it is the sense of rotation of the rotor 1 which determines which of the two cams 22, 23 is engaged by the cam 24. The sense of rotation of the rotor 21 is indicated by arrows in FIGS. 6, 7. The two grooves 22, 23 forming the cams join each other at the end of the rotor 21 opposite the housing opening 2. A sampling movement and a pricking movement may begin from the same starting position in the illustrated embodiment.

Figure 8:
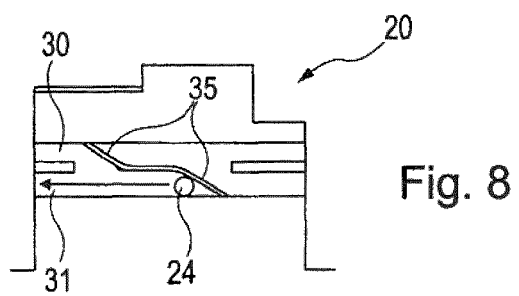
FIG. 8 shows another embodiment of a motion control, in the condition immediately before a pricking operation.

FIG. 8 shows another embodiment of a motion control 20 by which different movements of the coupling part 11 can be achieved for a pricking movement and for a sampling movement. Just as the motion control of the embodiment illustrated in FIGS. 6 and 7, the motion control 20 of the embodiment illustrated in FIG. 8 uses two different cams 30, 31. However, the cams 30, 31 are not disposed in the lateral surface of a rotor, but in a guide element that extends in the pricking direction. A routing device determines which of the cams 30, 31 is to be engaged by the cam rider 24. The routing device 35 comprises legs, which are in contact with the lateral walls of the groove and which can be lifted off those lateral walls and can then be restored to their initial position illustrated in FIG. 8 by the action of a spring.

Figure 9:
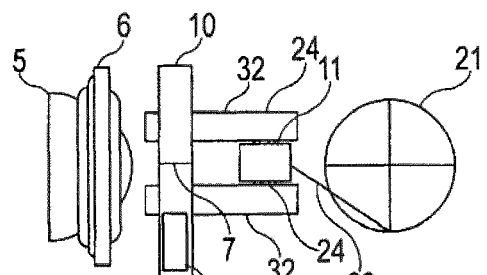
FIG. 9 shows a diagrammatic cross-sectional representation of the pricking system, prior to a pricking operation, according to FIG. 8.

A diagrammatic representation of a pricking system with a motion control 20 is illustrated in FIG. 9. The coupling part 11 of that embodiment is arranged between two guide elements 32 with cams 30, 31, respectively, which are engaged by the cam riders 24. Although in principle a single such guide element 32 with cams 30, 31 would be sufficient, tilting moments can be reduced by the use of two guide elements 32 with cams 30, 31.

In the case of the illustrated pricking system the coupling part 11 is driven via a rotor 21 with which the coupling part is connected via a connecting rod 33. The rotor 21 is connected with a mechanical energy storage mechanism, for example a spiral spring, which provides the required motive force when a pricking or a sampling movement is initiated.

FIG. 9 shows the coupling part 11 in its starting position, prior to a pricking operation. A lancet 7 of the carrier tape 10 is located in the pricking position so that it can prick a body part 5, applied to the housing opening 2, by actuation of the drive 21. The corresponding starting position of the cam rider 24 is illustrated in FIG. 8.

Figure 10:
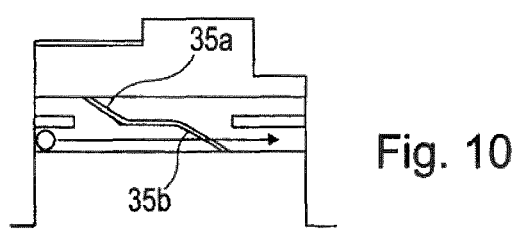
FIG. 10 shows a representation according to FIG. 8 during a pricking operation.
Figure 11:
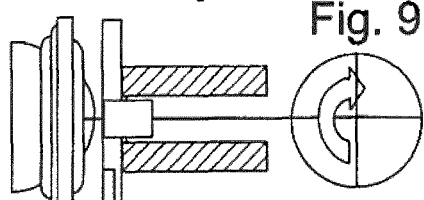
FIG. 11 shows a representation according to FIG. 9 during a pricking operation.
Figure 12:
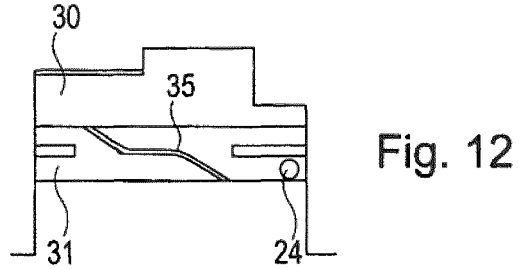
FIG. 12 shows a representation according to FIG. 10, immediately after a pricking operation has been performed.
Figure 13:
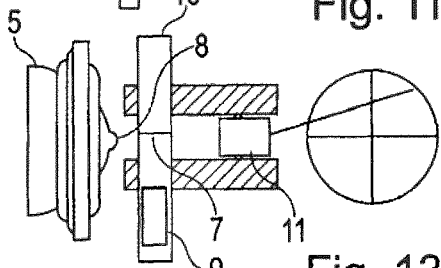
FIG. 13 shows a representation according to FIG. 11, immediately after a pricking operation has been performed.

When a pricking movement is initiated, the cam rider 24 moves linearly in the direction indicated by the arrow in FIG. 8 so that the coupling part 11 also moves linearly from its illustrated starting position into the end position illustrated in FIG. 11 from which it will be returned to the starting position illustrated in FIG. 13 by a restoring movement. The end position of the cam rider 24 reached by that movement is illustrated in FIG. 10. During the restoring movement from the end position illustrated in FIG. 10 or 11, the leg 35b of the routing means 35 is momentarily lifted off the cam rider so that the cam rider is permitted so slide below the routing device and into its starting position illustrated in FIG. 12, for a sampling movement.

Figure 15:
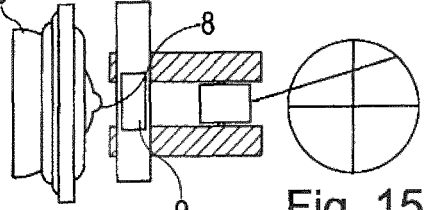
FIG. 15 shows a representation according to FIG. 13, prior to a sampling movement.

FIG. 13 shows the coupling part after a pricking operation, in its starting position for a sampling movement. It also shows body liquid issuing from the prick wound produced. The lancet 7, having just been moved for a pricking operation, is still in its correct position for use. By moving the carrier tape 10 in its longitudinal direction, a test field 9 is moved into the correct position for use, as illustrated in FIG. 15.

Figure 14:
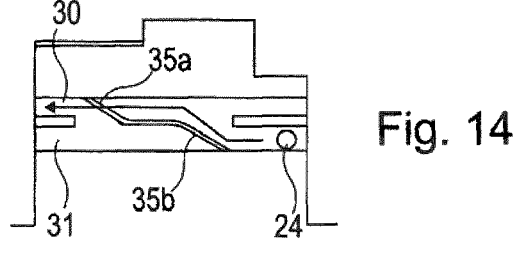
FIG. 14 shows a representation according to FIG. 8, prior to a sampling movement.

In FIG. 14, the path traveled by the cam rider 24 in a sampling movement is indicated by an arrow. The routing device 35 ensures that the cam rider is deflected from the lower cam 31 as seen in the drawing—into the upper cam 30. The leg 35a is momentarily deflected toward the bottom during a sampling movement so that the cam rider 24 can reach its end position in the upper cam 30 for collection of a sample, as illustrated in FIG. 16.

Figure 16:
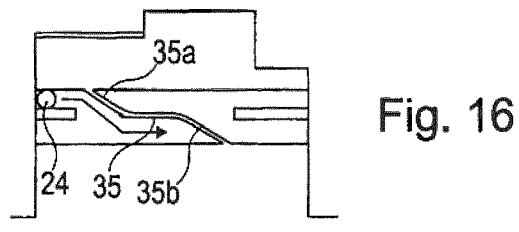
FIG. 16 shows a representation according to FIG. 14, at the moment, of a sampling operation.
Figure 17:
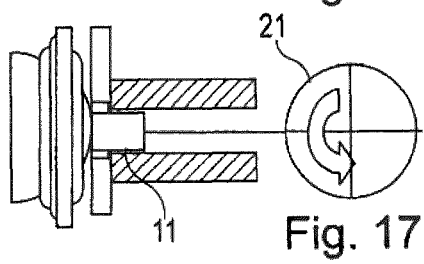
FIG. 17 shows a representation according to FIG. 15, at the moment of a sampling operation.

Corresponding to FIG. 16, FIG. 17 shows the coupling part 11 in its end position in which the carrier tape 10 is bent in lengthwise direction so that the longitudinal edges of the carrier tape 30 have approached each other. The bent condition of the carrier tape 10 causes the test field 9 to come into spacious contact with the body part 5 for collection of a sample of a body liquid.

Figure 18:
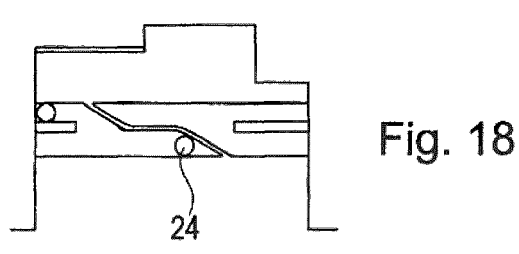
FIG. 18 shows a representation according to FIG. 16, after a sampling operation.
Figure 19:
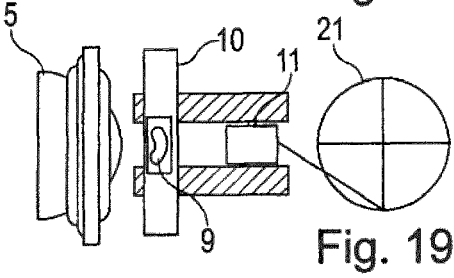
FIG. 19 shows a representation according to FIG. 17, after a sampling operation.

FIG. 18 shows the cam rider 24 after it has been returned from the end position illustrated in FIG. 16. The starting position illustrated in FIG. 18 corresponds to the starting position illustrated in FIG. 8. Correspondingly, FIG. 19 shows the coupling part 11 returned to its starting position, as well as a test field 9 with an absorbed sample of body liquid.

Figure 20:
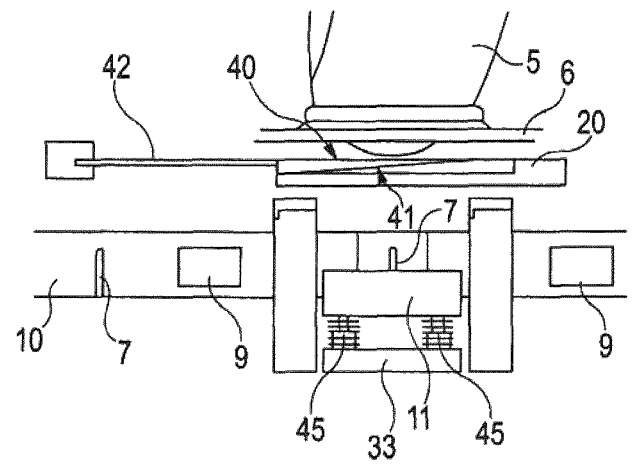
FIG. 20 shows a cross-sectional view of another embodiment of a motion control.

FIG. 20 shows another embodiment of the motion control 20 which provides that the end position reached by the coupling part 11 in a sampling movement is laterally offset relative to the end position reached by the coupling part 11 in a pricking movement. The lateral offset occurs transversely to the transport direction of the illustrated carrier tape 10 and transversely to the pricking direction.

Figure 21:
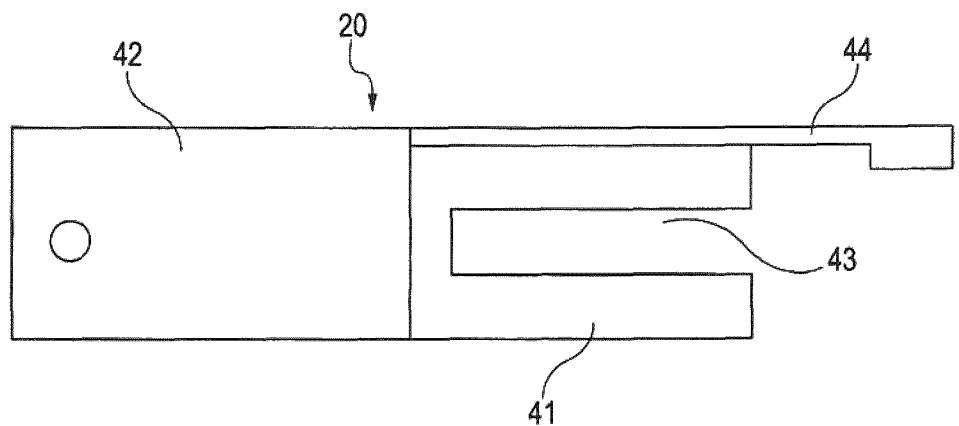
FIG. 21 shows a top view, taken in the pricking direction, of the motion control of FIG. 20.
Figure 22:
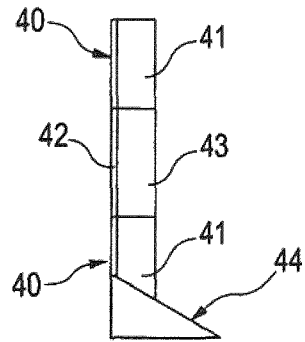
FIG. 22 shows a front view of the embodiment of FIG. 20.
Figure 23:
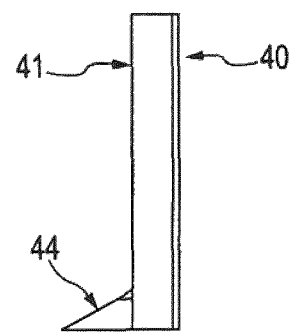
FIG. 23 shows a rear view of the embodiment of FIG. 20.

In the embodiment illustrated in FIG. 20, the motion control 20 uses a stop element, illustrated in FIG. 21 by a top view taken in the pricking direction, in FIG. 22 by a front view and in FIG. 23 by a rear view. The stop element 20 can be adjusted transversely to the pricking direction, in the illustrated embodiment in the transport direction of the carrier tape 10. As will be discussed in more detail below, the stop element 20 serves to limit the pricking depth in the position illustrated in FIG. 20, where it is located for a pricking operation.

The stop element 20 has a bottom surface 40, facing the housing opening 2, and an upper surface with a stop surface 41, extending obliquely to the bottom surface 40, against which the coupling part 11 comes to abut when performing a pricking operation. The stop element 20 has an extension in the pricking direction, from the stop surface 41 to the bottom surface 40, that varies transversely to the pricking direction with the result that the length by which the tip of the lancet 7 will project beyond the bottom surface 40 of the stop element during the pricking operation can be adjusted by moving the stop element 20 transversely to the pricking direction. The stop element 20 is coupled, via an extension 42, with an adjusting means by which it can be displaced transversely to the pricking direction, in the transport direction of the carrier tape 10, for adjusting the pricking depth.

As can be seen in FIG. 21, a slot 43 is disposed in the stop element 20. That slot 43 extends through the stop surface 41 so that a lancet 7 will project through the slot 41 in a pricking operation.

As can be seen especially in FIGS. 22 and 23, the stop element 20 comprises an inclined surface 44 extending obliquely to the pricking direction. During a sampling movement the stop element 20 is displaced transversely to the pricking direction by a length sufficient to ensure that the coupling part 11 will hit upon the inclined surface 44 that extends in the transport direction. The inclined surface thus forms a deflection plane along which the coupling part slides being thereby deflected transversely to the pricking direction and transversely to the transport direction. This likewise provides the possibility to obtain a lateral offset between the end position of the coupling part in a sampling movement and the end, position of the coupling part in a pricking movement.

The drive of the embodiment illustrated in FIG. 20 can be similar to the drive of the embodiment illustrated in FIG. 9, i.e. it may be configured as a rotor drive being coupled with the coupling part 11 via a connecting rod. As the coupling part 11 can be prematurely stopped by the stop surface 41 of the stop surface 20 during a pricking movement, it is connected with the connecting rod 33 via one or more compensation springs 45. For a small pricking depth, the thrust produced by the connecting rod 33 is balanced out by the compensating springs 45 so that blocking of the drive is prevented.

In the illustrated embodiment, the deflection plane 44 preferably extends over a length at least equal to the length of the coupling part 11 in the transport direction. The stop element 20 cooperates with an abutment (not shown) that absorbs the force exerted by a coupling part 11 as it slides along the deflected plane 44, and thus stabilizes the deflection part against displacement transversely to the pricking direction. The abutment additionally may serve to urge the bottom surface of the stop element 20 against the body part 5 in which a prick wound is to be produced.

Just as the motion control of the embodiments described before, the motion control constituted by the stop element 20 and the deflection plane 44 connected with it has the result to laterally displace the end position of the coupling part 11 during a sampling movement relative to the end position of the coupling part 11 during a pricking movement by approximately 10-40% of the width of the carrier tape 11, preferably 15-35%, especially 20-30% of the width of the carrier tape 10. In the embodiment illustrated in FIG. 20, the lateral displacement amounts to ¼ of the width of the carrier tape 10. When the carrier tape 10 is folded for sampling along its middle, in lengthwise direction, the resulting displacement is such that the carrier tape 10 will project beyond each side of the prick wound by a quarter of its width.

Figure 24:
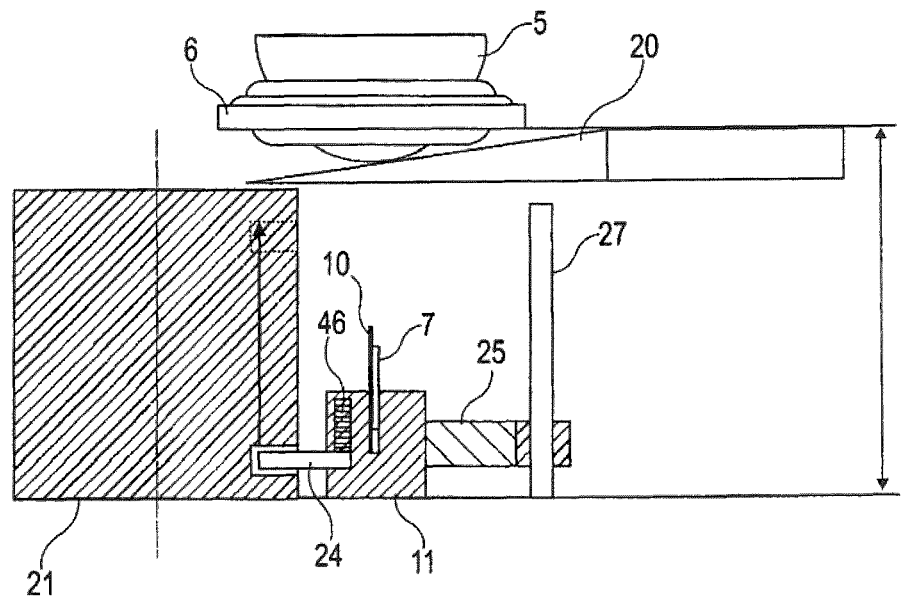
FIG. 24 shows another embodiment with a coupling part in a starting position for a pricking movement.

FIG. 24 shows another embodiment of the pricking system where, just as in the embodiment described before, the pricking depth can be adjusted by means of a wedge-shaped stop element 20. FIG. 24 shows the coupling part 11 in its starting position for a pricking movement. As in the embodiment discussed with reference to FIGS. 6 and 7, the drive 21 comprises a rotor with a groove disposed on a cylindrical lateral surface, which acts as a cam that is engaged by a earn rider 24 of the coupling part 11.

Figure 25:
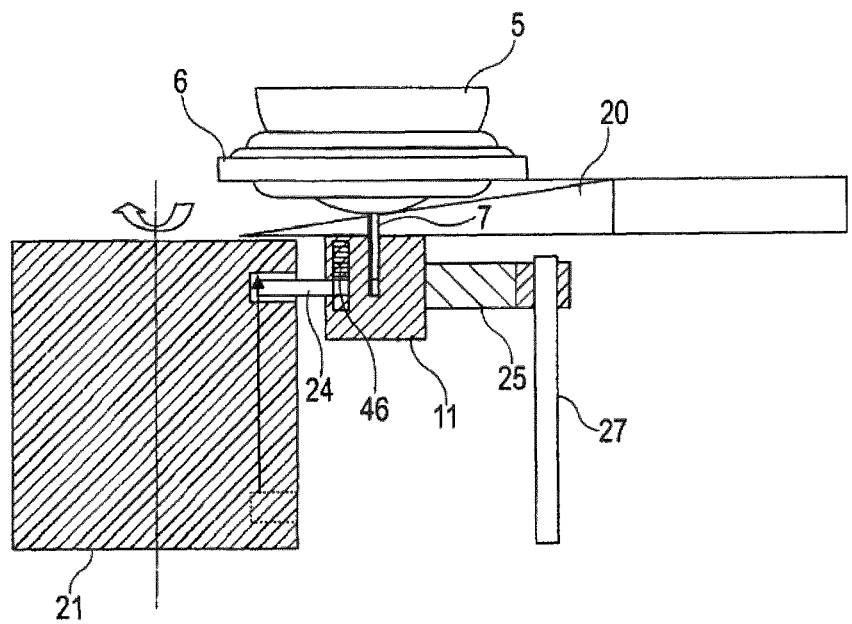
FIG. 25 shows a representation according to FIG. 24, with the coupling part in its end position of a pricking movement.

During a pricking movement the coupling part 11 is moved in the pricking direction by rotation of the rotor 21 until in its end position illustrated in FIG. 25 it hits upon the stop element 20 the position of which defines the pricking depth of a lancet 7 when pricking a body part 5 that has been applied to the housing opening. In order to ensure that the rotation of the rotor 21 can always be completed, even when the coupling part 11 his upon the stop element 20, the cam rider 24 is coupled with the coupling part 11 via a compensating spring 46 acting in the pricking direction. When the coupling part 11, performing a pricking movement, reaches its end position illustrated in FIG. 25 by hitting upon the stop element 20, the rotor 21 continues to rotate so that the cam rider 24 continues to move in the pricking direction. That movement is balanced out by the compensating spring 46, which is compressed during that process. Irrespective of the position of the stop element 20, the cam rider 24 therefore always travels the same length in a pricking movement. In contrast, the travel of the coupling part 11 is defined by the position of the stop element 20.

Figure 26:
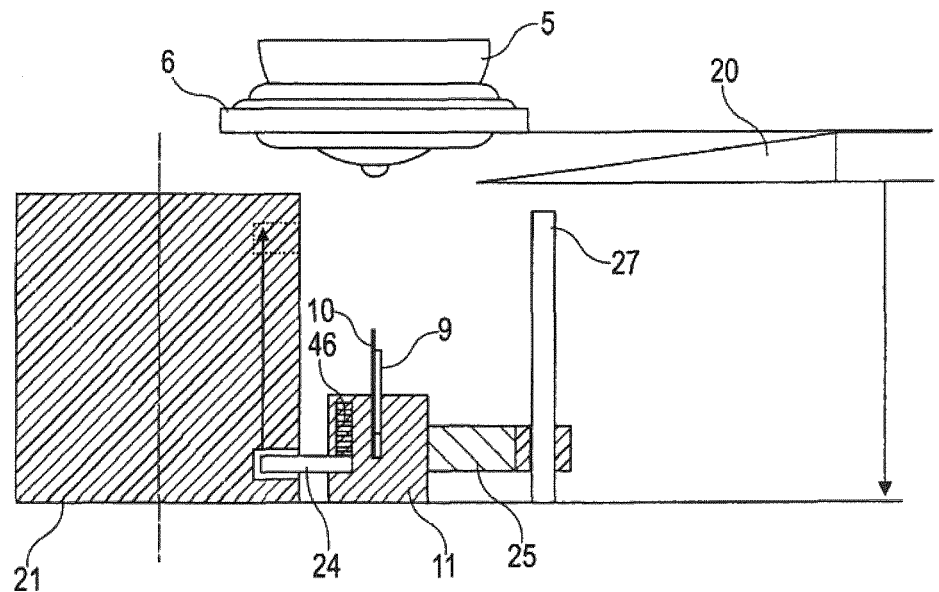
FIG. 26 shows a representation according to FIG. 24, with a coupling part in its starting position for a sampling movement.
Figure 27:
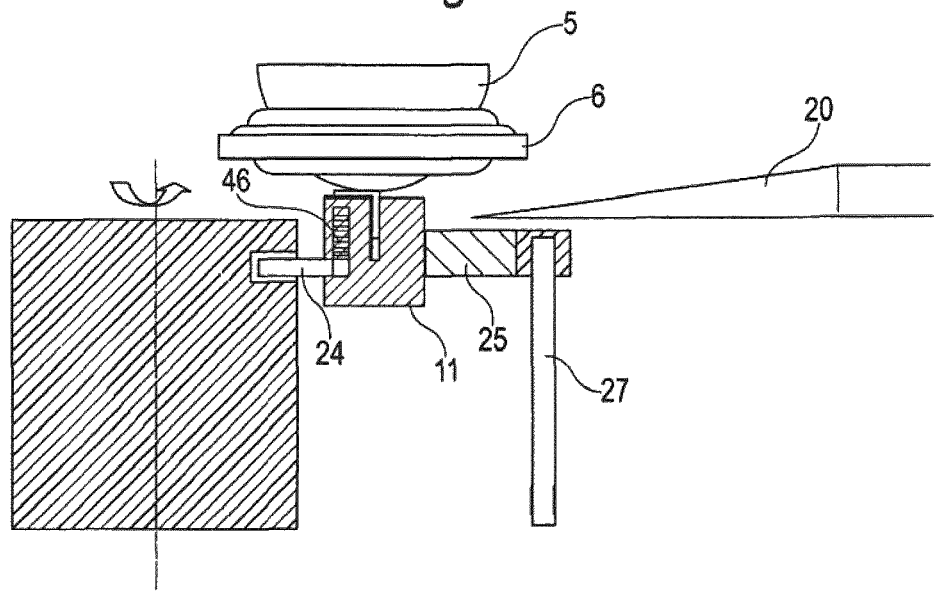
FIG. 27 shows a representation according to FIG. 24, with the coupling part in its end position of a sampling movement.

For collecting a sample, the stop element 20 is moved out of the path of the coupling part 11, transversely to the pricking direction, so that the coupling part 11 is free during a sampling movement to move over the full travel of the cam arranged on the lateral surface of the rotor 21. FIG. 26 shows the coupling part 11 in its starting position for a sampling movement. FIG. 27 shows the coupling part 11 correspondingly in its end position in a sampling operation.

The stop element 20 may be additionally provided with an inclined surface 44, as illustrated in FIGS. 21 to 23, for effecting a deflection of the coupling part 11 transversely to the pricking direction in a sampling movement. For the sake of clarity, that inclined surface 44 is not shown in FIGS. 26 and 27. The rotor 21, the coupling part 11 and the guide 27 may be carried on a common base so that those parts can be deflected together by an inclined surface 44, transversely to the pricking direction.

List Of Reference Numerals
1 Pricking system
2 Housing opening
3 Operating elements
4 Display device
5 Body part
6 Housing
7 Lancet
8 Body liquid
9 Sampling device
10 Carrier tape
11 Coupling part
20 Motion control
21 Drive
22 Cam
23 Cam
24 Cam rider
25 Spring
26 Guide
27 Rail
30 Cam
31 Cam
32 Guide element
33 Connecting rod
35 Routing device
35a, b Leg of the routing device
40 Bottom surface
41 Stop surface
42 Extension
43 Slot
44 Deflection plane
45 Compensating spring
46 Compensating spring Having described the invention in detail and by reference to specific embodiments thereof, it will be apparent that modifications and variations are possible without departing from the scope of the invention defined in the appended claims. More specifically, although some aspects of the present invention are identified herein as preferred or particularly advantageous, it is contemplated that the present invention is not necessarily limited to these preferred aspects of the invention.

The invention claimed is:

1. A pricking system comprising:
lancets for producing a prick wound;
sampling devices for collecting a sample of a body fluid from the prick wound;
a housing having an opening for application of a body part in which the prick wound is to be produced;
a drive arranged in the housing for moving one of the lancets to produce the prick wound and to then move one of the sampling devices to the prick wound so produced;
a coupling part for coupling to the drive one of the lancets for a pricking movement and then coupling to the drive one of the sampling devices for a sampling movement, the coupling part being moved, during the pricking movement and the sampling movement, respectively, from a starting position into an end position by an advancing movement, and from the end position back into the starting position by a reversing movement, respectively; and
a motion control which, during the sampling movement, causes the coupling part to reach an end position that differs from the end position reached by the coupling part during the pricking movement, wherein the end position reached by the coupling part in the sampling movement is laterally displaced relative to the end position reached by the coupling part in the pricking movement.

2. The pricking system of claim 1 wherein the coupling part performs a longer travel in the sampling movement than in the pricking movement.

3. The pricking system of claim 1 further comprising a transport facility for transporting one of the sampling devices to the coupling part after a pricking operation by moving the sampling device in a transport direction.

4. The pricking system of claim 3 wherein the coupling part reaches the end position in the sampling movement that is displaced transversely to the transport direction relative to the end position reached by the coupling part in the pricking movement.

5. The pricking system of claim 1 wherein the sampling device comprises a test field with test chemicals for testing the collected sample of the body fluid.

6. The pricking system of claim 1
wherein the lancets and the sampling devices are arranged on a carrier tape.

7. The pricking system of claim 6 wherein the carrier tape is bent in lengthwise direction during the pricking movement and during the sampling movement.

8. The pricking system of claim 6 wherein the motion control comprises a cam control with a first cam for the pricking movement and a second cam for the sampling movement.

9. The pricking system of claim 6 wherein the motion control comprises a deflection plane which can be adjusted transversely to the pricking direction and which extends obliquely to the pricking direction in order to deflect the coupling part transversely to the pricking direction by sliding along the deflection plane.

10. The pricking system of claim 9, wherein the deflection plane is connected with an adjusting element for adjusting the pricking depth, which element comprises a bottom surface, facing the body part during the pricking operation, and an upper surface with a stop surface against which the coupling part abuts during a pricking operation, the stop element having an extension in the pricking direction, from the stop surface to the bottom surface, that varies transversely to the pricking direction with the result that the length by which the tip of one of the lancets will project beyond the bottom surface of the stop element during the pricking operation can be adjusted by moving the stop element transversely to the pricking direction.

11. The pricking system of claim 6 wherein the coupling part is laterally deflected during the advancing step of the sampling movement.

12. The pricking system of claim 6 wherein the housing comprises a receptacle for an exchangeable supply of lancets and sampling devices.

* * * * *